(12) United States Patent
Kuge et al.

(10) Patent No.: US 8,603,829 B2
(45) Date of Patent: Dec. 10, 2013

(54) ATHEROSCLEROSIS MARKER AND USE THEREOF

(75) Inventors: Yuji Kuge, Hokkaido (JP); Hiroko Hanzawa, Tokorozawa (JP); Takeshi Sakamoto, Asaka (JP); Naomi Manri, Kawagoe (JP)

(73) Assignee: Hitachi Ltd., Tokyo (JP)

( * ) Notice: Subject to any disclaimer, the term of this patent is extended or adjusted under 35 U.S.C. 154(b) by 35 days.

(21) Appl. No.: 12/805,619

(22) Filed: Aug. 10, 2010

(65) Prior Publication Data

US 2011/0065199 A1    Mar. 17, 2011

(30) Foreign Application Priority Data

Sep. 9, 2009   (JP) ................................. 2009-208639

(51) Int. Cl.
*G01N 33/50*    (2006.01)
(52) U.S. Cl.
USPC ............................ 436/86; 436/63; 530/387.1
(58) Field of Classification Search
USPC ............... 436/63, 71, 86, 173, 536, 808, 811; 422/430; 435/2, 7.1, 11, 810; 530/387.1; 250/281, 282
See application file for complete search history.

(56) References Cited

U.S. PATENT DOCUMENTS

2007/0099251 A1*   5/2007   Zhang et al. .................. 435/7.23
2008/0085526 A1*   4/2008   Gangadharan et al. ....... 435/7.92

FOREIGN PATENT DOCUMENTS

JP   2001-525058   12/2001
WO   WO 98/43630   10/1998

OTHER PUBLICATIONS

Koenig, Wolfgang et al., "Biomarkers of Atherosclerotic Plaque Instability and Rupture", American Heart Association, Arterioscler Thromb Vasc Biol 2007, vol. 27, pp. 15-26.
Bowen, Michael A. et al., "Characterization of Mouse AKCAM (CD166): the CD6-Binding Domain is Conserved in Different Homologs and Mediates Cross-Species Binding", Eur. J. Immunol 1997, vol. 27, pp. 1469-1478.
Arai, Sakato et al., "A Role for the Apoptosis Inhibitory Factor AIM/Spα/Api6 in Atherosclerosis Development", Cell Metabolism, Mar. 2005, vol. 1, pp. 201-213.

* cited by examiner

*Primary Examiner* — Maureen Wallenhorst
(74) *Attorney, Agent, or Firm* — Stites & Harbison PLLC; Juan Carlos A. Marquez, Esq.; Stephen J. Weyer

(57) ABSTRACT

A method is provided for diagnosing or predicting atherosclerosis with the use of, as indicators, markers (factors) that allow early detection and progression prediction of the disease and a method for evaluating preventive or therapeutic effects. In one form, the present method includes detecting CD166 (ALCAM) level in a sample of a subject such as human. Another aspect of the present method includes evaluating preventive or therapeutic effects of a compound on atherosclerosis. A kit and an apparatus for carrying out such methods is also provided.

9 Claims, 8 Drawing Sheets

Fig. 1

```
         10          20          30          40          50          60
MASKVSPSCR  LVFCLLISAA  VLRPGLGWYT  VNSAYGDTIV  MPCRLDVPQN  LMFGKWKYEK
         70          80          90         100         110         120
PDGSPVFIAF  RSSTKKSVQY  DDVPEYKDRL  SLSENYTLSI  ANAKISDEKR  FVCMLVTEDN
        130         140         150         160         170         180
VFEAPTLVKV  FKQPSKPEIV  NKAPFLETDQ  LKKLGDCISR  DSYPDGNITW  YRNGKVLQPV
        190         200         210         220         230         240
EGEVAILFKK  EIDPGTQLYT  VTSSLEYKTT  RSDIQMPFTC  SVTYYGPSGQ  KTIYSEQEIF
        250         260         270         280         290         300
DIYYPTEQVT  IQVLPPKNAI  KEGDNITLQC  LGNGNPPPEE  FMFYLPGQPE  GIRSSNTYTL
        310         320         330         340         350         360
TDVRRNATGD  YKCSLIDKRN  MAASTTITVH  YLDLSLNPSG  EVTKQIGDTL  PVSCTISASR
        370         380         390         400         410         420
NATVVWMKDN  IRLRSSPSFS  SLHYQDAGNY  VCETALQEVE  GLKKRESLTL  IVEGKPQIKM
        430         440         450         460         470         480
TKKTDPSGLS  KTIICHVEGF  PKPAIHWTIT  GSGSVINQTE  ESPYINGRYY  SKIIISPEEN
        490         500         510         520         530         540
VTLTCTAENQ  LERTVNSLNV  SAISIPEHDE  ADDISDENRE  KVNDQAKLIV  GIVVGLLLAA
        550         560         570         580
LVAGVVYWLY  MKKSKTASKH  VNKDLGNMEE  NKKLEENNHK  TEA
```

Fig. 2

```
           10          20          30          40          50          60
    MAPLFNLMLA  ILSIFVGSCF  SESPTKVQLV  GGAHRCEGRV  EVEHNGQWGT  VCDDGWDRRD 70          80          90         100         110         120
    VAVVCRELNC  GAVIQTPRGA  SYQPPASEQR  VLIQGVDCNG  TEDTLAQCEL  NYDVFDCSHE
                                                *
          130         140         150         160         170         180
    EDAGAQCENP  DSDLLFIPED  VRLVDGPGHC  QGRVEVLHQS  QWSTVCKAGW  NLQVSKVVCR 190         200         210         220         230         240
    QLGCGRALLT  YGSCNKSTQG  KGPIWMGKMS  CSGQEANLRS  CLLSRLENNC  THGEDTWMEC
                      *                                  *
          250         260         270         280         290         300
    EDPFELKLVG  GDTPCSGRLE  VLHKGSWGSV  CDDNWGEKED  QVVCKQLGCG  KSLHPSPKTR 310         320         330         340         350         360
    KIYGPGAGRI  WLDDVNCSGK  EQSLEFCRHR  LWGYHDCTHK  EDVEVICTDF  DV
                      *
```

ATHEROSCLEROSIS MARKER AND USE THEREOF

CLAIM OF PRIORITY

The present application claims priority from Japanese patent application JP 2009-208639 filed on Sep. 9, 2009, the content of which is hereby incorporated by reference into this application.

BACKGROUND OF THE INVENTION

1. Field of the Invention

The present invention relates to a method for diagnosing or predicting atherosclerosis based on a variation of the expression of an atherosclerosis biomolecular marker, a method for evaluating preventive or therapeutic effects of a compound on atherosclerosis, and a kit and an apparatus for carrying out such methods.

2. Background Art

The term "arteriosclerosis" collectively refers to diseases characterized by artery wall thickening caused by a variety of factors such as aging and lifestyle habits, decreased artery elasticity, and luminal stenosis. Cardiovascular diseases, such as myocardial infarction, and cerebrovascular diseases, such as cerebral infarction and cerebral hemorrhage, are regarded as arteriosclerosis-related diseases. In particular, atherosclerosis lesions (atheroma, plaque) comprises stable lesions rich in calcified fibrous tissue and unstable lesions rich in lipid and inflammatory cells having a relatively high risk of rupture. It is shown that most acute clinical findings regarding myocardial infarction, cerebral infarction, and the like are resulted from unstable atherosclerosis lesions. Therefore, safe and simple diagnosis and prevention of atherosclerosis, and establishment of effective therapeutic methods therefor are urgent needs (Koenig W. and Khuseyinova N., Arterioscler. Thromb. Vasc. Boil., 27:15-26, 2007).

At present, arteriosclerosis is diagnosed by invasive methods including angiography, and intravascular ultrasound, or noninvasive methods including ultrasound (particularly for the carotid artery and the femoral artery). It is difficult to distinguish stable and unstable atherosclerosis lesions by angiography, while on the other hand, it is relatively easy to distinguish them by angioscopy. However, both techniques are highly invasive. Therefore, less-invasive methods including the use of PET (positron emission tomography) and CTA (computerized tomography angiography) are being discussed. In any case, the use of an expensive and specified determination apparatuses and facilities is unavoidable, and the above techniques are available only in a limited number of institutions. In addition, such techniques can not easily process a plurality of specimens in parallel and lacks general versatility. Meanwhile, a clinical in vitro diagnostic technique for quantification of biomolecular markers whose levels significantly vary in blood or urine in the cases of certain diseases is a less invasive and highly versatile technique. It allows parallel processing of a plurality of specimens with the use of reagent kits and this can be carried out at a relatively low cost. This method does not require a specific measurement apparatus or facility and thus can be used in a general medical care facility. Also for atherosclerosis diagnosis, the development of a clinical in vitro diagnostic technique with the use of molecular markers has been expected.

For clinical in vitro diagnosis of atherosclerosis, a combined evaluation method using a risk factor group including obesity, hypertension, and lifestyle habits, in addition to main factors such as lipid markers (high levels of serum total cholesterol and LDL cholesterol and a low level of HDL cholesterol) has been suggested. Also, the Japan Arteriosclerosis Society describes the method in "Guidelines for Treatment of Hyperlipidemia (Kohshikessyo Chiryo Guideline)." The method has been used for risk evaluation and patient management in clinical practice. In addition, the relationship between variations in lipid markers and ischemic stroke has also been revealed. It is suggested that lipid markers can be used as indicators for the development of systemic arteriosclerosis in coronary arteries, cerebral arteries, and peripheral arteries and for the progression of lesions. However, there have been reports of a plurality of cases of patients with histories of myocardial infarction or with 50% coronary arterial stenosis discovered by a diagnostic method such as coronary angiography among patients whose laboratory values of lipid markers fell within the normal range and who were not found to have any specific risk factors. Therefore, the use of novel markers such as proteins and peptide molecules, in addition to lipid markers, has been discussed. For instance, CRP (C-reactive protein) is a protein showing a significant variation in a case involving an acute coronary artery disease. The blood CRP level increases up to as high as 300 μg/ml after 6 to 8 hours of the onset of the disease. Therefore, the applied use of CRP as a diagnosis marker in clinical practice for an ischemic heart disease or an unstable atherosclerosis lesion has been discussed (International Publication WO 98/43630; JP Patent Publication No. 2001-525058 A). However, it has been reported based on mass clinical analysis in Europe that evaluation with CRP alone is difficult due to its low specificity. Therefore, it is an important object to search for more specific protein/peptide molecular diagnosis markers with high levels of disease specificity and to use such markers in clinical practice.

CD166 (activated leukocyte cell adhesion molecule; ALCAM) is an immunoglobulin superfamily protein, which is a single-transmembrane protein belonging to the scavenger receptor cysteine rich superfamily. CD116 was identified as a CD6 ligand molecule. CD116 is known to be widely expressed in tissues and cells such as thymic epithelial cells, leukocytes, mesenchymal stem cells, and liver, pancreas, and brain tissues, and it regulates the intercellular signal transduction mechanism. It is thought that CD116 is widely present in humans, rodents, birds, zebrafish, and the like, regardless of species, and functions therein in a similar manner (Bowen M. A. et al., Eur. J. Immunol., 27:1469-1478, 1997). CD116 is also known to be expressed in cancer cells or tissues including prostate cancer, colorectal cancer, and melanoma, as well as other tissues, and to be involved in cancer metastasis. However, there are still no reports suggesting the involvement of CD116 in arteriosclerosis or unstable atherosclerosis lesions. Meanwhile, CD5L (apoptosis inhibitor expressed by macrophage; AIM) is a protein belonging to the scavenger receptor cysteine rich superfamily. CD5L was identified as a macrophage apoptosis inhibitory factor. Thereafter, it has been found that the arteriosclerosis lesion area significantly decreases in LDLR/CD5L double-deficient mice, which are arteriosclerosis-induced models, compared with LDLR-deficient mice, suggesting the involvement of CD5L in arteriosclerosis (Arai S. et al., Cell Metabolism, 1:201-213, 2005).

SUMMARY OF THE INVENTION

Development of arteriosclerosis has been problematic not only in middle-aged and senior adults but also in young adults along with changes in lifestyle habits and the social structure. If it becomes possible to adequately evaluate potential risks of developing atherosclerotic lesions that cause arteriosclerosis and serious diseases, the following can be expected: prevention of a disease through the improvement of lifestyle habits or the like, early diagnosis, prevention of progression and deterioration (severity) of the disease, and therapeutic possibilities. In addition, the above can serve as a clue for solving problems associated with the issues of efficient allocation of the medical expenses and financial burdens related to medical expenses in the future super-aging society. Therefore, the development of a technique for appropriately and specifically predicting and determining risks associated with the development of arteriosclerosis (and particularly, risks of the development of atherosclerosis) has been awaited.

It is an object of the present invention to identify a novel biomarker whose blood level varies along with the progression of arteriosclerosis, and provide a method for diagnosing or predicting atherosclerosis using the marker as an indicator, and a method for evaluating preventive or therapeutic effects on atherosclerosis.

The present inventors collected plasma samples from wild-type mice and ApoE-deficient mice, which are likely to develop arteriosclerosis and in which progression of arteriosclerosis is promoted by the administration of a high-fat diet, analyzed the expression levels of proteins present in the plasma samples in a comprehensive manner by a mass spectrometer, and successfully identified a plurality of proteins including CD166 and CD5L, which significantly increase in ApoE mouse plasma. We conducted intensive studies based on the idea that variations in the blood CD166 and CD5L levels might relate to the development of atherosclerosis. As a result, we have found that the CD166 and CD5L levels in blood correlate with the development or progression (severity) of atherosclerosis, and that the risk of developing atherosclerosis, the degree of risk, and the probability of symptom progression can be evaluated with the use of, as indicators, the level of CD166 or the levels of both CD166 and CD5L in blood. These findings have led to the completion of the present invention.

Specifically, the present invention encompasses the following.

(1) A method for diagnosing or predicting atherosclerosis, which comprises determining the level of CD166 (ALCAM) in a sample of a subject.

(2) The method according to (1), wherein the subject is a human.

(3) The method according to (1) or (2), wherein the sample is serum or plasma.

(4) The method according to any one of (1) to (3), which further comprises determining the level of CD5L in the sample.

(5) The method according to (4), which further comprises:
determining the levels of CD166 and CD5L in samples of a healthy control group that has not developed atherosclerosis;
obtaining the value of the CD166 level of the subject relative to the CD166 level of the healthy control group and the value of the CD5L level of the subject relative to the CD5L level of the healthy control group; and
determining the risk of developing a vascular disorder associated with atherosclerosis for the subject based on the values as indicators.

(6) The method according to any one of (1) to (5), which further comprises determining at least one level of other atherosclerosis markers in the sample.

(7) A method for evaluating a preventive or therapeutic effect of a test compound on atherosclerosis, which comprises determining the level of CD166 level in a sample of a subject in need of prevention or treatment of atherosclerosis to which the test compound has been administered.

(8) The method according to (7), wherein the subject is a human.

(9) The method according to (7) or (8), wherein the sample is serum or plasma.

(10) The method according to any one of (7) to (9), which further comprises determining the level of CD5L in the sample.

(11) The method according to (10), which further comprises comparing the levels of CD166 and CD5L in samples of a group consisting of subjects in need of prevention or treatment of atherosclerosis to which the test compound has been administered with the levels of CD166 and CD5L in samples of a group consisting of subjects in need of prevention or treatment of atherosclerosis to which the test compound has not been administered.

(12) The method according to any one of (7) to (11), which further comprises determining at least one level of other atherosclerosis markers in the sample.

(13) A kit for diagnosing or predicting atherosclerosis or for evaluating a preventive or therapeutic effect of a test compound on atherosclerosis, which comprises a substance for determining the level, of CD166 as an atherosclerosis marker.

(14) The kit according to (13), which further comprises a substance for determining the level of CD5L as an atherosclerosis marker.

(15) The kit according to (13) or (14), which further comprises a substance for determining at least one level of other atherosclerosis markers.

(16) The kit according to any one of (13) to (15), wherein the substance for determining the level of the atherosclerosis marker level is an antibody.

(17) An apparatus for diagnosing or predicting atherosclerosis or for evaluating a preventive or therapeutic effect of a compound on atherosclerosis, which comprises means for determining the level of CD166 as an atherosclerosis marker.

(18) The apparatus according to (17), which further comprises means for determining the level of CD5L as an atherosclerosis marker.

(19) The apparatus according to (17) or (18), which further comprises means for determining at least one level of other atherosclerosis markers.

(20) The apparatus according to any one of (17) to (19), wherein the means comprise a mass spectrometer for determining the level of the atherosclerosis marker.

According to the present invention, a method for examining and analyzing the risk of developing arteriosclerosis and progressive symptoms in an appropriate and simple manner, and a reagent and a kit for carrying out such method are provided.

BRIEF DESCRIPTION OF THE DRAWINGS

FIG. 1 shows the entire amino acid sequence of mouse CD166. The underline represents a peptide sequence, which was identified by mass spectrometry in plasma of 25-week-old mice.

FIG. 2 shows the entire amino acid sequence of mouse CD5L. The underline represents a peptide sequence, which was identified by mass spectrometry in plasma of 25-week-old mice. The symbol "*" represents a predicted sugar-chain binding site.

DETAILED DESCRIPTION OF THE INVENTION

Figure 3:
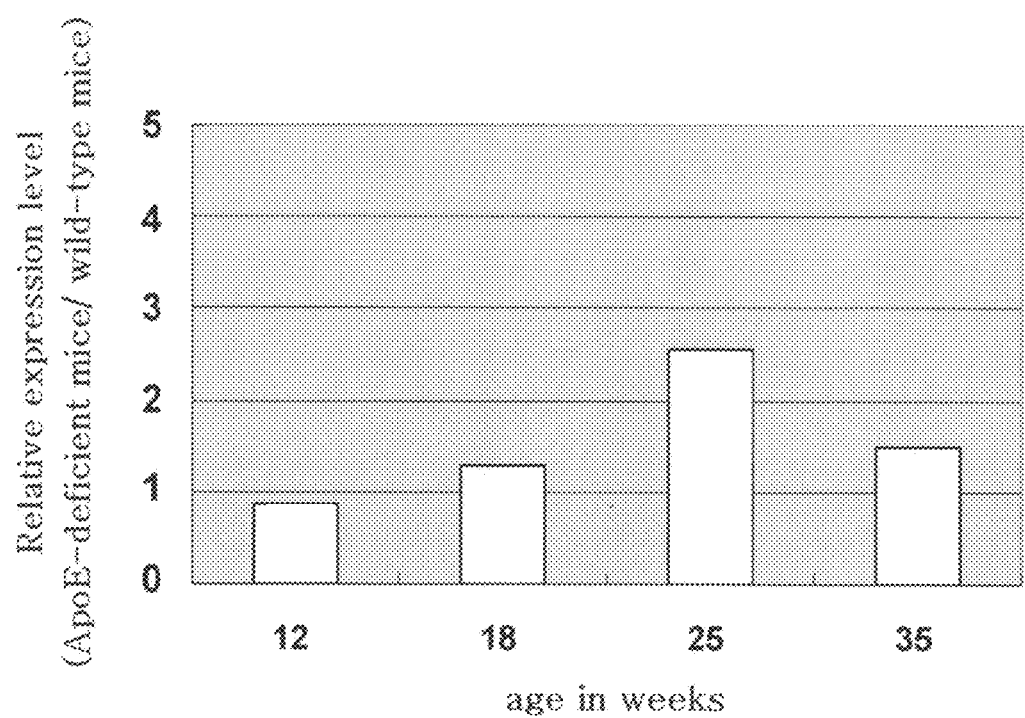
FIG. 3 shows the correlation between age in weeks and value of the mouse plasma CD166 expression level in ApoED mice relative to that in WT mice. The level was determined with the use of an anti-CD166 antibody.

The present invention has been completed based on the findings that the level (e.g., concentration) of CD166 alone or the levels of both CD166 and CD5L in a subject's sample significantly correlates with atherosclerosis, which is difficult to predict the time of the onset. According to the present invention, it is possible to determine the degree of possibility of the onset of atherosclerosis based on the levels obtained by determining the level of CD166 alone or the levels of both CD166 and CD5L in a sample of a subject. Therefore, CD166 and CD5L can be used as indicators for the risk of onset. Specifically, CD166 and CD5L can be used as atherosclerosis markers and therefore can be used for early detection of the disease. For instance, if the CD166 concentration in a sample of a subject exceeds a given reference value, it is interpreted that the subject has a high risk of the onset of atherosclerosis. In addition, if the CD166 concentration in a sample of a subject remains higher than the reference value and, at the same time, the CD5L concentration in the sample exceeds the reference value, it is interpreted that there is a high possibility of the onset of atherosclerosis. Further, if the CD5L concentration in a sample of a subject remains higher than the reference value and, at the same time, the value of the CD166 concentration in the sample relative to the reference value tends to continuously increase, it is interpreted that atherosclerosis progresses (severe symptoms). In addition, it is possible to evaluate preventive or therapeutic effects of a compound on atherosclerosis by administering the compound to a subject in need of prevention or treatment of atherosclerosis and determining the CD166 level and, if necessary, the CD5L level in a sample of the subject.

The term "atherosclerosis" used herein refers to a state in which the following are experienced: formation of a lesion (plaque) due to accumulation of a sludgy atherosclerotic substance containing fat such as cholesterol on the intimas of relatively large arteries (e.g., aorta, cerebral arteries, and coronary arteries), gradual thickening of blood vessel walls, and, as a result, arterial lumen stenosis. In addition, by diagnosing or predicting atherosclerosis according to the present invention, it is also possible to diagnose or predict diseases induced by atherosclerosis, including vascular disorders associated with atherosclerosis and, in particular, cardiovascular diseases such as myocardial infarction, and cerebrovascular diseases such as cerebral infarction and cerebral hemorrhage.

Samples to be tested with the use of atherosclerosis markers according to the present invention are not particularly limited as long as they are collected from a subject. Preferably, blood specimens are used. Examples of blood specimens include whole blood, plasma, and serum, any of which may be used. If plasma is used, an anticoagulant publicly known in the art or a widely used anticoagulant, such as heparin or sodium citrate, may be used, and preferably EDTA may be used as an anticoagulant. After blood collection, storage in ice or chilled storage of the collected specimen is recommended.

CD166 (activated leukocyte cell adhesion molecule; ALCAM) is an immunoglobulin superfamily protein, which is a single-transmembrane protein belonging to the scavenger receptor cysteine rich superfamily. The amino acid sequence of CD166 is publicly known. An example thereof is the amino acid sequence shown in SEQ ID NO: 1 (FIG. 1). For example, the amino acid sequence of human CD166 is registered with Genbank under accession number NP-001618. According to the present invention, the CD166 level can also be obtained by determining the level of a CD166 peptide fragment. An example of such peptide fragment is a peptide fragment comprising the amino acid sequence of CSLIDK (SEQ ID NO: 3).

CD5L (apoptosis inhibitor expressed by macrophage; AIM) is a protein belonging to the scavenger receptor cysteine rich superfamily, which is a macrophage apoptosis inhibitory factor. The amino acid sequence of CD5L is publicly known. An example thereof is the amino acid sequence shown in SEQ ID NO: 2 (FIG. 2). For example, the amino acid sequence of human CD5L is registered with Genbank under accession number NP-005885. According to the present invention, the CD5L level can also be obtained by determining the level of a CD5L peptide fragment. An example of such peptide fragment is a peptide fragment comprising the amino acid sequence having any one of SEQ ID NOS: 4 to 43.

The levels of atherosclerosis markers (i.e., CD166 and CD5L) in a sample of a subject can be determined by any method which is known in the art and not particularly limited. Examples thereof include mass spectrometry and immunological methods. In addition, determination of the atherosclerosis marker levels in the present invention includes quantitative analysis of CD166 and, if necessary, CD5L in a sample and particularly determination of the CD166 concentration and; if necessary, the CD5L concentration in a sample.

For mass spectrometry, LC/MS analysis with high sensitivity is particularly advantageous. For example, when blood is used as a sample, a method comprising the following steps can be used: (1) a step of separating plasma from blood of a subject; (2) a step of labeling a plasma protein and/or peptide; (3) a step of fractionating plasma into a plasma protein and/or peptide; (4) a step of subjecting a plasma protein and/or peptide to mass spectrometry; and (5) a step of identifying labeled CD166 and, if necessary, CD5L based on mass spectrometry results. For labeling, a commercially available isotopic labeling reagent may be used. For fractionation, a commercially available strong cation-exchange (SCX) column can be used, which is preferable.

For immunological methods, a convenient method can be selected from among methods widely used in the art. Examples thereof include, but are not limited to, enzyme-linked immunosorbent assay (ELISA), double monoclonal antibody sandwich immunoassay (U.S. Pat. No. 4,376,110), monoclonal or polyclonal antibody sandwich assay, immunofluorescence, Western blotting, dot blotting, immunoprecipitation, protein chip analysis, two dimensional electrophoresis, and SDS-polyacrylamide electrophoresis.

For example, when blood is used as a sample, a method comprising the following steps can be used: (1) a step of separating plasma from a blood of a subject; (2) a step of fractionating plasma by SDS-polyacrylamide gel electrophoresis; (3) a step of transferring a protein on gel to a solid phase; (4) a step of reacting with an antibody (anti-CD166 antibody) capable of immunologically reacting with CD166 in a specific manner and, if necessary, with an antibody (anti-CD5L antibody) capable of immunologically reacting with CD5L in a specific manner; (5) a step of washing the solid phase; (6) a step of contacting a labeled antibody capable of immunologically reacting with the relevant antibody in a specific manner with the solid phase; (7) a step of washing the solid phase; and (8) a step of determining the CD166 level and, if necessary, the CD5L level based on the label. As a solid phase, a commercially available nitrocellulose membrane or PVDF membrane can be used. For labeling, an enzyme such as peroxidase or alkaline phosphatase, a fluorescent substance, and an avidin-biotin complex can be used.

An anti-CD166 antibody and an anti-CD5L antibody may be a monoclonal antibody or a polyclonal antibody. Commercially available antibodies may be used. An anti-CD166 antibody and an anti-CD5L antibody may be prepared by a method known in the art. The type of antibody globulin is not particularly limited and may be IgG, IgM, IgA, IgE, or IgD with IgG and IgM being preferred. The monoclonal antibody used in the present invention also includes: a "chimera" antibody (immunoglobulin) having a heavy chain and/or light chain consisting of one portion derived from a specific species or a specific antibody class or subclass and the remaining portion derived from a different species or a different antibody class or subclass; and antibody fragments such as Fab, $F(ab')_2$, and Fv fragments as long as an antibody fragment has a desired biological activity (U.S. Pat. No. 4,816,567).

A monoclonal antibody can be prepared by, for example, immunizing an animal with an immunogen, obtaining an antibody-producing cell, subjecting the cell to cell fusion with a myeloma cell to prepare a hybridoma having autonomous growth potential, selecting a clone producing an antibody having a desired specificity, culturing the clone cell, and purifying a secreted antibody. A polyclonal antibody can be prepared by, for example, immunizing an animal with an immunogen, and collecting blood from the animal to obtain anti-serum. As an immunogen, CD166, CD5L, or an immunogenic fragment thereof can be used. An immunogenic fragment preferably comprises an epitope. Examples thereof include a partial peptide containing at least 6 amino acids and preferably 8 to 50 amino acids. When a peptide fragment is used as an immunogen, it is preferable to use a peptide fragment that has been conjugated to a carrier protein such as KLH or BSA.

Preferably, the method for diagnosing or predicting atherosclerosis of the present invention can be carried out by determining reference levels of the CD166 level (e.g., the CD166 concentration) and, if necessary, the CD5L level (e.g., the CD5L concentration) in a sample, comparing the levels of a subject with the reference levels, and evaluating the levels of the subject. The reference levels can be determined based on the values obtained from a healthy animal or a subject to be tested. The term "healthy animal" refers to an animal that has not developed atherosclerosis. Preferably, the CD166 level and, if necessary, the CD5L level in a healthy control group (healthy animal group) are determined as the reference levels. For example, a diagnosis can be made based on significant increases in the CD166 concentration and, if necessary, the CD5L concentration compared to those in a healthy animal. In addition, for example, a diagnosis can be made based on significant increases in the CD166 concentration and, if necessary, the CD5L concentration in a subject compared to the initial levels in the subject in a healthy state. It is advantageous to make a diagnosis based on significant increases in the CD166 concentration and the CD5L concentration in a subject compared to those in a healthy animal or the initial levels in the subject for the improvement of accuracy of results.

Accordingly, in one embodiment, the diagnostic or predictive method of the present invention comprises: determining the levels of CD166 CD5L in samples of a healthy control group that has not developed atherosclerosis; and determining a risk of developing an atherosclerosis-associated vascular disorder for a subject with the use of, as indicators, the value of the CD166 level of the subject relative to the CD166 level of the healthy control group and the value of the CD5L level of the subject relative to the CD5L level of the healthy control group.

In addition, in relation to the development and progression of atherosclerosis, the blood CD5L concentration tends to increase so as to reach its peak earlier than the blood CD166 concentration. Therefore, it is possible to determine the degree of progression, severity, or stabilization of atherosclerosis in a subject by determining the levels of the two molecules in the subject over time. Further, it is also possible to determine the same by associating the level of CD166 alone or the levels of CD166 and CD5L with a different indicator such as a level of a known atherosclerosis marker(s). Examples of an atherosclerosis marker that can be associated with the above indicators include total cholesterol; LDL (low density lipoprotein), HDL (high density lipoprotein), triglyceride, blood sugar, hsCRP (high sensitivity CRP), and homocysteine.

The present invention relates to a method for evaluating preventive or therapeutic effects of a compound such as a drug on atherosclerosis. Specifically, a test compound is administered to a subject in need of prevention or treatment of atherosclerosis, followed by determination of the CD166 level and, if necessary, the CD5L level in a sample of the subject. Thus, preventive or therapeutic effects of the compound on atherosclerosis can be evaluated. More specifically, preventive or therapeutic effects of a test compound on atherosclerosis can be evaluated by comparing the CD166 level and the CD5L level in samples of a group consisting of subjects in need of prevention or treatment of atherosclerosis to which the test compound has not been administered with the CD166 level and the CD5L level in samples of a group consisting of subjects in need of prevention or treatment of atherosclerosis to which the test compound has been administered.

According to the present invention, a subject is preferably a mammal. The term "mammal" refers to warm-blooded vertebrates. Examples thereof include: primates such as humans and monkeys; rodents such as mice, rats, and rabbits; pet animals such as dogs and cats; and livestock such as bovines, horses, and pigs. The present invention is preferably used for primates and particularly for humans.

The present invention provides a kit for diagnosing or predicting atherosclerosis or evaluating preventive or therapeutic effects of a compound on atherosclerosis. The kit of the present invention comprises a substance for determining the level of CD166 as an atherosclerosis marker (for example, anti-CD166 antibody) and, if necessary, a substance for determining the level of CD5L as an atherosclerosis marker (for example, an anti-CDL5 antibody). The kit of the present invention can further comprise a buffer (for dilution or washing), a standard antigen, a labeled antibody capable of immunologically reacting with an anti-CD166 antibody or an anti-CD5L antibody in a specific manner, a substrate reagent capable of causing color development, luminescence, or fluorescence, and an instruction describing procedures and an evaluation method. Preferably, the kit is designed for convenient assay. Alternatively, as the above kit, a mass spectrometry reagent set designed to comprise an isotopic labeling reagent, a minicolumn for fractionation, a buffer, and an instruction can be provided.

In addition, the present invention provides an apparatus for diagnosing or predicting atherosclerosis or an apparatus for evaluating preventive or therapeutic effects of a compound on atherosclerosis. For example, such apparatus can determine the levels of CD166 and, if necessary, CDL5 as atherosclerosis markers, and it is preferably equipped with a mass spectrometer for such determination. An example of such apparatus is an apparatus composed of a measurement unit for detecting and digitalizing signals obtained from the mass spectrometer, and a data analysis unit comprising the software for processing measurement values and a calculator. Also, an apparatus composed of an optical measurement unit for detecting and digitalizing or imaging signals derived from color development, luminescence, or fluorescence, and a data analysis unit comprising the software for processing measurement values and a calculator can be used.

The present invention allows detection and prediction of atherosclerosis which has not been detected due to normal laboratory values obtained with the use of conventional clinical markers and lack of findings based on risk factors during the initial examination or health examination. In addition, the present invention allows risk detection and prediction for the examination of a probability of the development or progression of arteriosclerosis and a disease associated with arteriosclerosis. This is significantly useful for preventive medicine and public health. The use of the present invention allows the effective use of the levels of CD166" and CD5L obtained by measuring CD166 alone or CD166 and CD5L in a sample as indicators showing a risk of developing arteriosclerosis and a disease associated with arteriosclerosis and a probability of progression of arteriosclerosis. Therefore, the present invention can be used for the development of an appropriate and convenient risk test or analysis method, a variety of reagents and medicines, and a related apparatus for the examination of a probability of the development or progression of arteriosclerosis and a disease associated with arteriosclerosis.

The broad object, characteristics, and usefulness of the present invention described herein are apparently understood by persons skilled in the art based on descriptions of the present application. In addition, the descriptions of the present invention, which include preferred embodiments and specific examples of the present invention, are used merely for explanation. Therefore, persons skilled in the art would be able to readily understand to make changes or modifications to the present invention within the spirit and scope of the present invention based on knowledge disclosed herein. Further, all publications, patents, and patent applications cited herein are used for explanation and incorporated herein by reference in their entirety.

The present invention is hereafter illustrated in greater detail with reference to the following examples. The examples are provided merely for the explanation of the present invention and are not intended to limit or restrict the scope of the present invention disclosed herein. It is apparently understood that various changes and modifications to the present invention can be made based on the concept of the present invention.

EXAMPLES

Example 1

ApoE-deficient (ApoED) mice, which were deficient in the lipid metabolism-related protein ApoE, were used as atherosclerosis models. Administration of a high-fat diet causes lesion progression in ApoED mice. In addition, lesion progression is promoted depending on age in weeks. In 12-week-old mice, lesion progression is observed to such an extent that arterial intimal thickening and lipid accumulation are observed. In 18-week-old mice, lipid accumulation results in foam cell formation. In 25-week-old mice, many forms of unstable atherosclerotic plaque are widely observed in arteries, and this corresponds to the most dangerous stage in the atherosclerosis process. In 35-week-old mice, many stable lesions that are highly fibrotic and calcified lesions are observed. Therefore, in this example, 12, 18, 25, and 35-week-old wild-type (WT) mice and ApoED mice (male and female mice: 9 animals each) were subjected to blood collection. Plasma samples were prepared from the blood using 10% EDTA/2K solution.

Among the above plasma samples, plasma samples from 12-week-old and 25-week-old WT and ApoED mice were analyzed by mass spectrometry. Albumin, immunoglobulin, and transferrin in plasma were removed with the use of Multiple Affinity Removal Column for mouse plasma (Ms-3; 4.6×100 mm; Cat. No. 5188-5218; Agilent), followed by measurement of protein concentration and isotopic labeling with Cleavable Isotope-Coded-Affinity-Tag (cICAT) reagent (cICAT® Reagent 10-assay Kit; Cat. No. 4339036; Applied Biosystems). The plasma samples of WT and ApoED mice (1 mg each) that had been treated with the Affinity Removal Column were adjusted in a manner such that each sample contained 6M urea, 0.05% SDS, 50 mM Tris (pH 8.5), 5 mM EDTA, 10 mM TBP (final concentrations) in a total volume of 800 µl, followed by degeneration treatment at 37° C. for 30 minutes. A "Light cICAT reagent" and a "Heavy cICAT reagent," each of which had been dissolved with acetonitrile (200 µl), were added to a WT sample and an ApoED sample, respectively, followed by a labeling reaction at 37° C. for 2 hours. A 10 mM Tris buffer (pH 8.0) was added to each sample for pH adjustment. A trypsin solution (Trypsin, TPCK Treated; Cat. No. 4352157; Applied Biosystems) (160 µl) adjusted to 125 µg/ml was added thereto. Then, both types of samples were mixed in equivalent volumes, followed by a trypsin digestion reaction at 37° C. for 16 hours. Further, peptide fragments obtained by trypsin treatment were applied into SCX column (poly Sulfoethyl A; 4.6×100 mm; PolyLC Inc.), followed by separation of the eluate into 25 fractions. Separation was carried out with the use of an eluent A [10 mM $KH_2PO_4$ (pH 2.8), 25% ACN] and an eluent B [10 mM $KH_2PO_4$ (pH 2.8), 25% ACN, 0.5 M KCl] with a linear gradient (% B: 10 minutes-0%, 70 minutes-20%, 85 minutes-50%, 90 minutes-60%, 95 minutes-60%, and 100 minutes-100%). Each fraction was subjected to vacuum concentration so as to result in a volume that was approximately one-fourth (¼) of the initial volume. Then, desalting with a desalting column (CAPCELL C18 MG; 2.0×10 mm; Shiseido) and vacuum drying were performed. An eluent A (2% ACN, 0.05% trifluoroacetic acid (TFA)) and an eluent B (80% ACN, 0.05% TFA) were used for desalting.

Each SCX fraction was analyzed using a mass spectrometry apparatus and an accompanying LC system device (NanoFrontier LD; Hitachi High-Technologies Corporation). Each obtained sample was dissolved in a buffer A (water: 98%; ACN: 2%; formic acid: 0.1%) (4 to 10 µl). One microliter of each obtained solution was applied into the apparatus. A MonoCap for Fast-flow (50 µm ϕ×150 mm; C18; GL Sciences) was used as a sample separation column in the LC system. Analysis was carried out with a linear gradient of a buffer A and a buffer B (water: 2%; ACN: 98%; formic acid: 0.1%) at a flow rate of 200 mL/min, provided that the buffer B concentration reached 2% to 30% in 120 minutes. A Monolith Trap (50 µm ϕ×150 mm; Cat. No. C18-50-150; Hitachi High-Technologies Corporation) was used as a trap column in the apparatus. A quartz spray chip (Picotip; outer diameter: 360 µm; inner diameter: 50 µm; tip inner diameter: 10 µm; New Objective) was used as a column tip. Electrospray ionization mass spectrometry was performed in the positive ion mode. Samples obtained from 25 fractions were subjected twice to IBA (information based Acquisition) analysis. IBA is a technique involving storing target information (m/z, charge number, retention time) obtained by the first analysis in a database within an apparatus, and analyzing ions that do not correspond to the target information in the second analysis. It was expected that weak ions would be analyzed with the use of such technique so as to increase the number of identified plasma proteins. The following are additional apparatus conditions: Curtain Gas Flow: 0.7 L/min; Spray potential: 1700 V; Detector potential: 2200 V; Isolation Time: 5 ms; Isolation Width: 10 Da; and CID Time: 10 ms. The measurement data were processed using software that had been developed for ICAT comparative quantification. Thus, comparative analysis data for two groups (the WT group and the ApoED group) were obtained.

As a result, among approximately 180 types of plasma proteins identified by mass spectrometry, CD166 and CD5L were found to have significantly increased in the ApoED group compared with the WT group. The results are shown in Table 1. The expression of CD166 was not confirmed in 12-week-old mice fed with a normal diet and in those fed with a high-fat diet. However, both male and female groups consisting of 25-week-old mice in the ApoED group showed increased expression levels 5 times as great as that shown in the WT group. This strongly suggests the involvement of CD166 in atherosclerotic plaque formation in atherosclerosis. Table 2 lists peptide fragments of CD166, which levels were found to increase in plasma samples of 25-week-old mice in the ApoED group by mass spectrometry. In FIG. 1, the underline represents the position of a peptide identified in Table 2 in the entire amino acid sequence of mouse CD166.

TABLE 1

Expression levels of CD166 and CD5L in ApoED plasma relative to those in WT plasma
Relative expression level (ApoE-deficient/Wild type)

|  | Age in weeks | Feed | Male group analysis 1 (M1) | Male group analysis 2 (M2) | Female group analysis 1 (F1) | Female group analysis 2 (F2) | Mean value | Standard deviation |
|---|---|---|---|---|---|---|---|---|
| CD166 | 12 | Normal diet | N.D.* | N.D. | N.D. | N.D. | N.D. | N.D. |
|  |  | High-fat diet | N.D. | N.D. | N.D. | N.D. | N.D. | N.D. |
|  | 25 | High-fat diet | 4.54 | 4.92 | 7.13 | 7.77 | 5.93 | 1.60 |
| CD5L | 12 | Normal diet | 2.24 | 2.37 | 2.07 | 1.98 | 2.16 | 0.18 |
|  |  | High-fat diet | 5.87 | 4.80 | 3.72 | 3.61 | 4.50 | 0.84 |
|  | 25 | High-fat diet | 4.80 | 4.40 | 4.74 | 5.24 | 4.78 | 0.34 |

*N.D.: Not detected

TABLE 2

CD166 peptide fragments identified in plasma samples of 25-week-old mice

| Uni-prot KB Entry Name (Accession Number) |  | Peptide Sequence | Start Sequence | Stop Sequence | Ratio (ApoED/WT) | Retention Time (min) | Precursor Mass (m/z) |
|---|---|---|---|---|---|---|---|
| CD166_MOUSE (Q61490) | M1 | CSLIDK | 313 | 318 | 4.54 | 31.06 | 453.245 |
|  | M2 | CSLIDK | 313 | 318 | 5.13 | 22.77 | 305.518 |
|  | F1 | CSLIDK | 313 | 318 | 7.63 | 28.89 | 457.778 |
|  | F2 | CSLIDK | 313 | 318 | 9.84 | 18.62 | 305.516 |

The ApoED group consisting of 12-week-old mice fed with a normal diet showed an increased CD5L expression level twice as great as that shown in the relevant WT group. The ApoED group consisting of 12-week-old mice fed with a high-fat diet showed an increased CD5L expression level 4.5 times as great as that shown in the relevant WT group. The ApoED group consisting of 25-week-old mice fed with a high-fat diet showed an increased CD5L expression level 4.8 times as great as that shown in the relevant WT group. These results suggest the involvement of CD5L in abnormal lipid metabolism, which can be a cause of atherosclerosis. Table 3 lists CD5L peptide fragments that were found to have increased in the ApoED group by mass spectrometry. In addition, the underline shown in FIG. 2 represents the positions of peptides of the entire amino acid sequence of mouse CD5L, such peptides being identified as listed in Table 3.

TABLE 3

CD5L peptide fragments identified in plasma samples of 25-week-old mice

| Uni-Prot KB Entry Name (Accession Number) | | Peptide Sequence | Start Sequence | Stop Sequence | Ratio (ApoED/ WT) | Retention Time (min) | Precursor Mass (m/z) | Calculated Mass (Da) | Seq ID No. |
|---|---|---|---|---|---|---|---|---|---|
| CD5L_MOUSE (Q9QWK4) | M1 | DVAVVCR | 60 | 66 | 5.08 | 24.83 | 494.788 | 987.517 | 4 |
| | | ELNCGAVIQTPR | 67 | 78 | 6.33 | 46.78 | 768.941 | 1535.818 | 5 |
| | | LVDGPGHCQGR | 143 | 153 | 5.28 | 11.39 | 458.912 | 1373.692 | 6 |
| | | VEVLHQSQWSTVCK | 154 | 167 | 4.00 | 45.43 | 940.463 | 1878.971 | 7 |
| | | ALLTYGSCNK | 187 | 196 | 4.60 | 38.72 | 648.837 | 1295.654 | 8 |
| | | SCLLSR | 220 | 225 | 4.54 | 31.06 | 453.245 | 904.480 | 9 |
| | | LVGGDTPCSGR | 248 | 258 | 5.20 | 22.25 | 649.349 | 1296.654 | 10 |
| | | LVGGDTPCSGRLEVLHK | 248 | 264 | 5.03 | 46.59 | 505.028 | 2016.087 | 11 |
| | | GSWGSVCDDNWGEKEDQVVCK | 265 | 285 | 3.11 | 62.19 | 938.405 | 2812.293 | 12 |
| | | IWLDDVNCSGKEQSLEFCR | 310 | 328 | 3.70 | 72.57 | 905.409 | 2713.334 | 13 |
| | M2 | DVAVVCR | 60 | 66 | 4.18 | 19.08 | 499.273 | 996.547 | 14 |
| | | ELNCGAVIQTPR | 67 | 78 | 5.36 | 40.73 | 509.930 | 1526.787 | 15 |
| | | LVDGPGHCQGR | 143 | 153 | 4.20 | 9.23 | 458.904 | 1373.692 | 16 |
| | | VEVLHQSQWSTVCK | 154 | 167 | 4.41 | 41.67 | 627.341 | 1878.971 | 17 |
| | | ALLTYGSCNK | 187 | 196 | 3.00 | 32.93 | 653.346 | 1304.685 | 18 |
| | | MSCSGQEANLR | 209 | 219 | 4.65 | 19.91 | 716.325 | 1430.669 | 19 |
| | | SCLLSR | 220 | 225 | 4.52 | 26.66 | 453.237 | 904.480 | 20 |
| | | LVGGDTPCSGR | 248 | 258 | 4.48 | 17.08 | 649.333 | 1296.654 | 21 |
| | | LVGGDTPCSGRLEVLHK | 248 | 264 | 4.28 | 41.57 | 505.039 | 2016.087 | 22 |
| | | IWLDDVNCSGKEQSLEFCR | 310 | 328 | 4.03 | 69.92 | 905.470 | 2713.334 | 23 |
| | | EQSLEFCR | 321 | 328 | 4.34 | 36.54 | 624.293 | 1246.606 | 24 |
| | F1 | DVAVVCR | 60 | 66 | 3.68 | 22.67 | 494.784 | 987.517 | 25 |
| | | ELNCGAVIQTPR | 67 | 78 | 4.29 | 42.69 | 768.945 | 1535.818 | 26 |
| | | LVDGPGHCQGRVEVLHQSQWSTVC | 143 | 167 | 4.96 | 50.40 | 809.687 | 3234.652 | 27 |
| | | VEVLHQSQWSTVCK | 154 | 167 | 4.48 | 44.35 | 627.337 | 1878.971 | 28 |
| | | ALLTYGSCNK | 187 | 196 | 4.66 | 36.61 | 653.374 | 1304.685 | 29 |
| | | MSCSGQEANLR | 209 | 219 | 5.02 | 23.92 | 716.348 | 1430.669 | 30 |
| | | SCLLSR | 220 | 225 | 6.08 | 28.89 | 457.778 | 913.510 | 31 |
| | | LVGGDTPCSGR | 248 | 258 | 5.27 | 21.63 | 649.362 | 1296.654 | 32 |
| | | LVGGDTPCSGRLEVLHK | 248 | 264 | 4.53 | 43.36 | 673.044 | 2016.087 | 33 |
| | | GSWGSVCDDNWGEKEDQVVCK | 265 | 285 | 4.11 | 59.40 | 938.482 | 2812.293 | 34 |
| | | IWLDDVNCSGKEQSLEFCR | 310 | 328 | 4.42 | 69.04 | 905.495 | 2713.334 | 35 |
| | F2 | ELNCGAVIQTPR | 67 | 78 | 6.42 | 42.93 | 769.007 | 1535.818 | 36 |
| | | LVDGPGHCQGR | 143 | 153 | 4.49 | 9.02 | 687.868 | 1373.692 | 37 |
| | | VEVLHQSQWSTVCK | 154 | 167 | 3.85 | 43.30 | 627.352 | 1878.971 | 38 |
| | | MSCSGQEANLR | 209 | 219 | 6.15 | 23.11 | 716.328 | 1430.669 | 39 |
| | | SCLLSR | 220 | 225 | 6.70 | 18.62 | 305.516 | 913.510 | 40 |
| | | LVGGDTPCSGR | 248 | 258 | 5.98 | 20.82 | 649.424 | 1296.654 | 41 |
| | | LVGGDTPCSGRLEVLHK | 248 | 264 | 4.13 | 42.82 | 505.063 | 2016.087 | 42 |
| | | IWLDDVNCSGKEQSLEFCR | 310 | 328 | 4.54 | 70.08 | 905.405 | 2713.334 | 43 |

Example 2

Plasma proteins prepared in Example 1 were subjected to immunological analysis with the use of SDS-polyacrylamide gel, an anti-CD166 antibody, and an anti-CD5L antibody. Each plasma protein (9 μg per lane) was introduced into SDS polyacrylamide gel (Cat. No. ET-520L; ATTO Corporation) and subjected to electrophoresis at a constant electric current of 20 mA for 90 minutes with a migration buffer (25 mM Tris, pH 8.3, 192 mM glycine, 0.1% SDS). The gel was introduced into a blotting apparatus (Horiz-Blot Cat. No. AE6687; ATTO Corporation) immediately after migration, followed by blot transfer at a constant electric current of 3.2 mA per 1 cm$^2$ of a PVDF membrane for 40 minutes with the use of a transfer buffer (25 mM Tris, 192 mM glycine, 20% Methanol). After transfer, the PVDF membrane was blocked in a blocking buffer (Cat. No. 37525; Pierce/Thermo Scientific) with shaking at room temperature for 60 minutes. As a primary antibody, an anti-mouse CD166 antibody (Cat. No. MAB1172; R&D Systems) or an anti-mouse CD5L antibody (Cat. No. MAB2834; R&D Systems) that had been diluted 1:5000 in a blocking buffer was used, and the membrane was incubated with the antibody with shaking at room temperature for 90 minutes. Unreacted antibodies were washed with a washing buffer (0.05% Tween 20, TBS). Then, a secondary antibody reaction was carried out by applying an alkaline phosphatase-labeled anti-IgG antibody (Cat. No. S3831; Promega) that had been diluted 1:5000 in the blocking buffer to the membrane and incubating at room temperature for 90 minutes. After washing with the above washing buffer, a chromogenic substrate for alkaline phosphatase (Cat. No. S3841; Promega) was added to obtain signals. After color development, the PVDF membrane was subjected to an image analyzer (ChemiDoc XRS; Bio-Rad). Each staining image was captured, followed by quantification of signal intensity with the use of the analysis software (Quantity One; Bio-Rad) included with the analyzer.

FIG. 3 shows results of experiments with the use of the anti-mouse CD166 antibody. The expression level of CD166 in mouse plasma in the ApoED group relative to that in the WT group increased in 12-week-old to 25-week-old mice. The expression level reached its peak in 25-week-old mice and then decreased in older mice. Such tendency corresponded well to atherosclerosis lesion progression in arteries of the ApoED mice. This strongly suggests that changes in the CD166 level in plasma correlate to atherosclerotic plaque formation.

Figure 4:
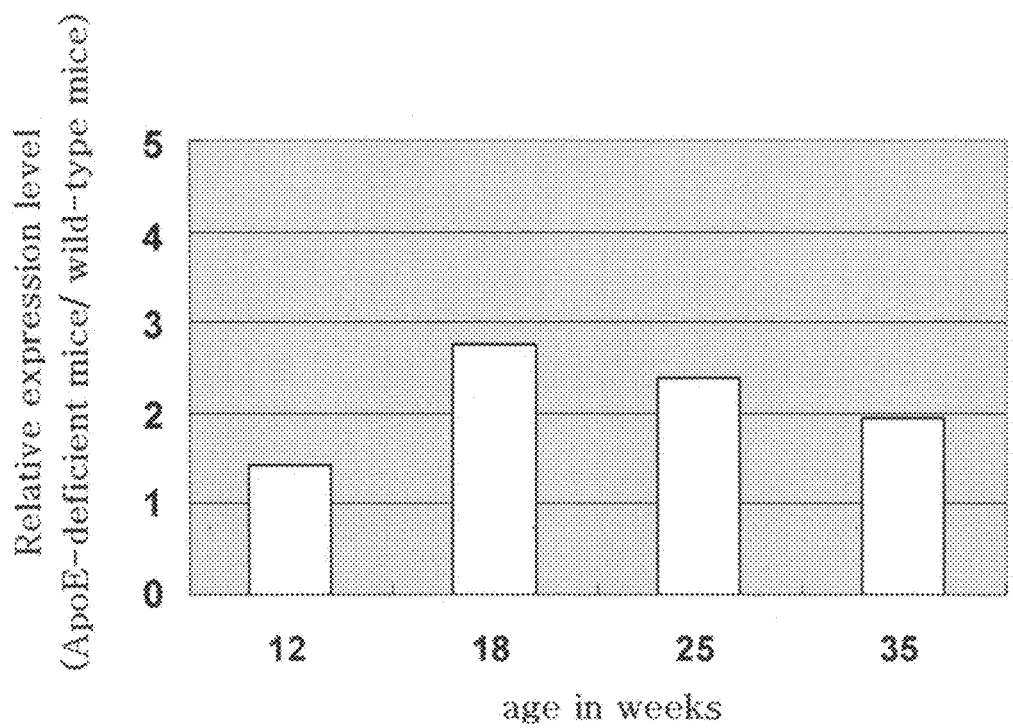
FIG. 4 shows the correlation between age in weeks and value of the mouse plasma CD5L expression level in ApoED mice relative to that in WT mice. The level was determined with the use of an anti-CD5L antibody.

FIG. 4 shows results of experiments with the use of the anti-mouse CD5L antibody. The CD5L expression level in mouse plasma in the ApoED group relative to that in the WT group increased in 12-week-old to 18-week-old mice. The expression level reached its peak in 18-week-old mice and then decreased. Such tendency partially corresponded to atherosclerosis lesion progression in arteries of the ApoED mice. This reveals that changes in the plasma CD5L level do not directly correlate to atherosclerotic plaque formation; however, such changes are presumed to be involved in early lesion formation to some extent.

Figure 5:
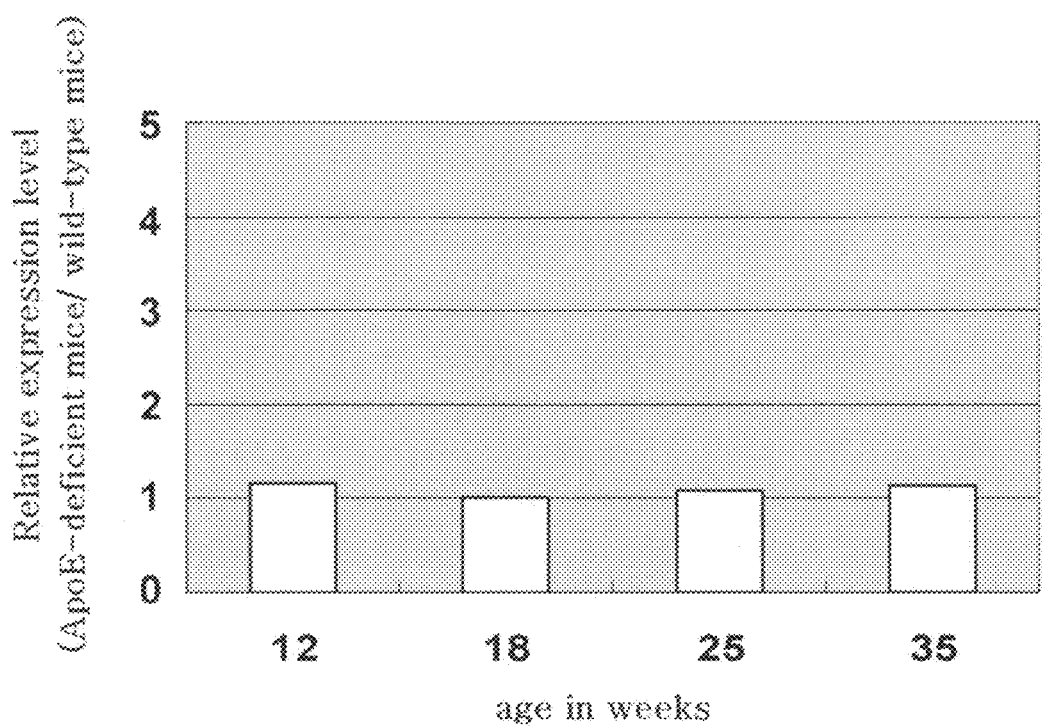
FIG. 5 shows the correlation between age in weeks and value of the mouse plasma CRP expression level in ApoED mice relative to that in WT mice. The level was determined by ELISA.

Next, the CRP level in mouse plasma was analyzed with the use of an ELISA kit (Cat. No. MB-KT095; MBL). Mouse plasma was diluted 1:20 in a diluent included with the kit. The diluted solution was added to wells of a 96-well plate with a CRP standard reagent, a positive control, and a negative control. A reaction was carried out in accordance with manufacturer's instructions. Thereafter, the absorbance at 450 nm was determined to obtain the CRP concentration. The results are shown in FIG. 5. There were no differences among mice in terms of the CRP expression level in mouse plasma in the ApoED group relative to that in the WT group. The relative expression level was almost unchanged in 12-week-old to 35-week-old mice. This tendency did not correspond to the atherosclerosis lesion progression in arteries of the ApoED mice. It was found that changes in the plasma CRP level of mice in the chronic state do not correlate to atherosclerotic plaque formation.

Example 3

Plasma samples were obtained from human specimens and CD166 and CD5L levels were determined in the samples. Table 4 summarizes sex, age, total cholesterol, LDL, HDL, and triglyceride levels for specimens. In particular, for the specimen A, the levels of total cholesterol, LDL cholesterol, and triglyceride were found to be high and the HDL cholesterol level was found to be low. Accordingly, the relevant subject was suspected to have a disease. The subject actually had a history of medication with simvastatin. Meanwhile, for the specimen D, the total cholesterol, LDL cholesterol, and triglyceride levels were low compared with the other specimens. The levels were similar to those of healthy individuals.

TABLE 4

|  | Specimen A | Specimen B | Specimen C | Specimen D |
|---|---|---|---|---|
| Sex | Male | Male | Male | Male |
| Age | 51 | 30 | 54 | 47 |
| Total cholesterol (mg/dL) | 296 | 236 | 192 | 174 |
| LDL cholesterol (mg/dL) | 153 | 155 | 97 | 92 |
| HDL cholesterol (mg/dL) | 36 | 41 | 49 | 52 |
| Triglyceride (mg/dL) | 536 | 198 | 232 | 148 |

Figure 6:
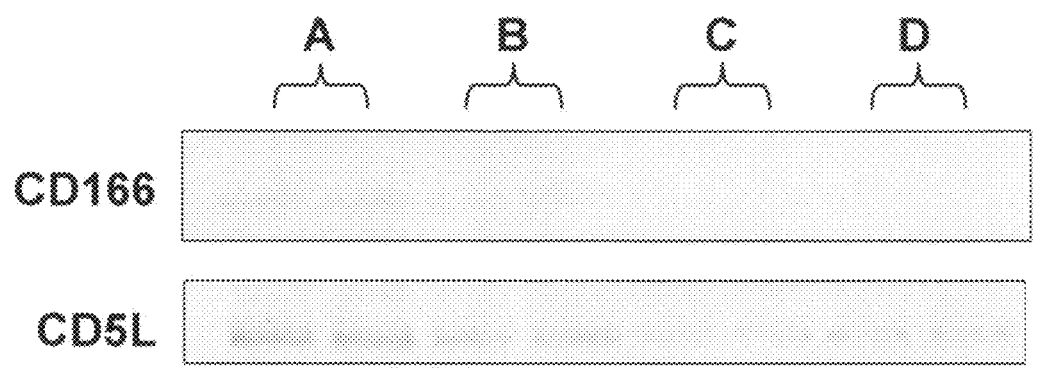
FIG. 6 shows results of detection of CD166 and CD5L in human plasma.

The concentrations of plasma proteins in the samples from the specimens listed in Table 4 were determined. Each plasma protein (9 µg per lane) was subjected to SDS-polyacrylamide electrophoresis. After transfer to a nitrocellulose membrane, the membrane was blocked in a blocking solution (0.1% BSA, TBS). An anti-human CD166 antibody (Cat. No. AF656; R&D Systems) or an anti-human CD5L antibody (Cat. No. AF2797; R&D Systems) that had been diluted 1:5000 in the blocking solution was applied onto the membrane, followed by washing with a TBS solution containing 0.05% Tween. Then, an alkaline phosphatase-labeled anti-IgG antibody (Cat. No. V1151; Promega) was applied onto the membrane. After washing, a chromogenic substrate was added for signal visualization. The results are shown in FIG. 6. Signals derived from an anti-human CD166 antibody were strongly detected in the specimen A. This strongly suggests a high risk of developing atherosclerosis. In addition, signals derived from an anti-human CD5L antibody were relatively strong in the specimen A, among the specimens A to D. This corresponds to the above results. That is, it is obviously understood that both CD166 and CD5L increase in a case involving atherosclerosis; however, CD166 is more sensitive than CD5L.

Example 4

Figure 7:
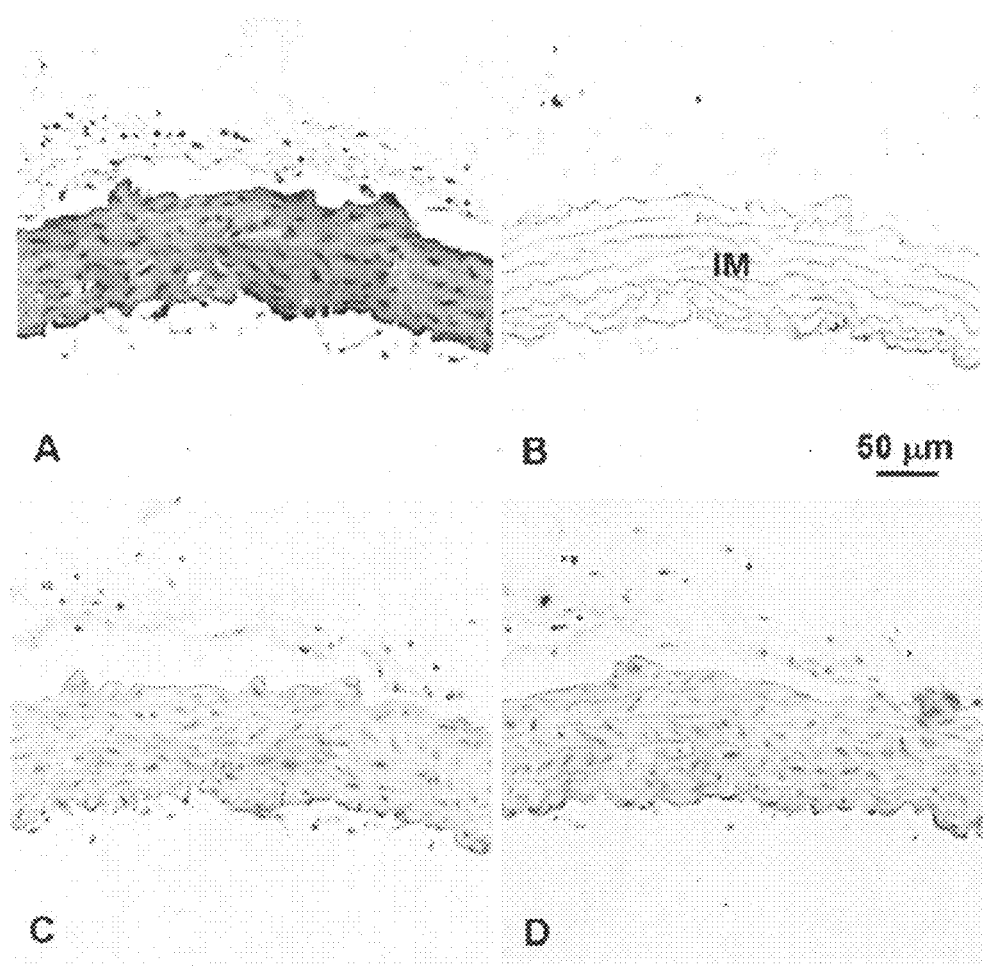
FIG. 7 shows results of tissue staining for aorta tissues from 25-week-old WT mice. A shows a hematoxylin-eosin staining image, B shows an oil red staining image, C shows an immunostaining image with an anti-CD166 antibody, and D shows an immunostaining image with an anti-CD5L antibody.
Figure 8:
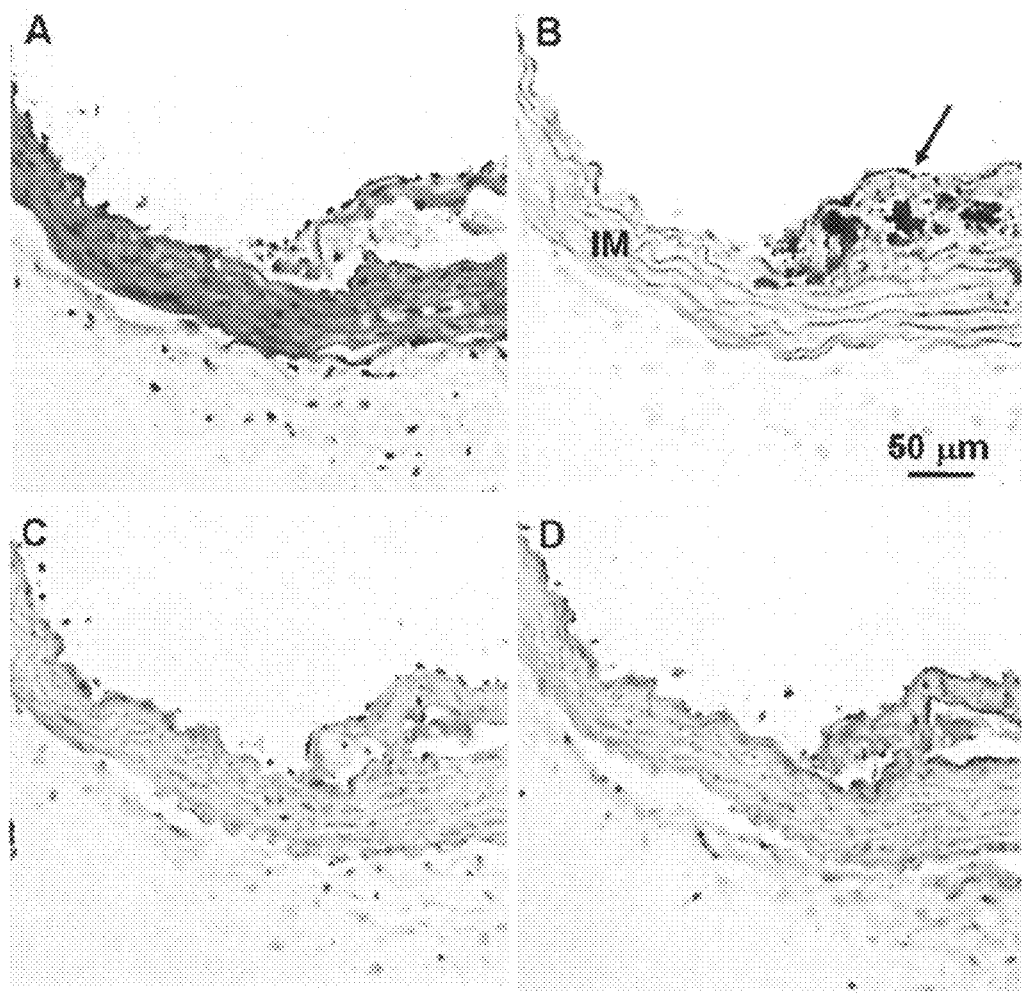
FIG. 8 shows results of tissue staining for mouse aorta tissues from 25-week-old ApoED mice. A shows a hematoxylin-eosin staining image, B shows an oil red staining image, C shows an immunostaining image with an anti-CD166 antibody, and D shows an immunostaining image with an anti-CD5L antibody.

Aorta tissue samples excised from 25-week-old WT and ApoED mice were subjected to 10% formalin fixation. Then, a section was excised from each sample at the aortic arch level, and frozen embedded blocks were prepared. Each block was sliced to a thickness of 3 µm, followed by hematoxylin-eosin staining, oil red staining, and immunostaining with an anti-CD166 antibody and an anti-CD5L antibody. An anti-CD166 antibody (a 1:50 dilution, Cat. No. AF1172; R&D Systems) and an anti-CD5L antibody (a 1:100 dilution, Cat. No. ab45408; Abcam) were used as primary antibodies. After reaction with a biotin-labeled secondary antibody, signal visualization was carried out with the addition of DAB. Stained samples were observed with a microscope (Biozero, BZ-8000; Keyence Corporation). Digital data of the obtained images were stored. FIG. 7 shows tissue staining images of the WT mouse aorta. No lesions were observed in a resulting image (FIG. 7: A). No accumulation of triglyceride particles was observed in a resulting image (FIG. 7: B). Results of antibody staining for CD166 and CD5L were found to be negative and the expression of both proteins was not confirmed (FIG. 7: C and D). FIG. 8 shows tissue staining images of ApoED mouse aorta. In the lesion indicated with the arrow, accumulation of triglyceride particles was observed in the form of red spots (FIG. 8: A and B). At the same time, CD166- and CD5L-derived signals were observed as brown spots inside the lesion. The expression of both proteins was confirmed (FIG. 8: C and D). The above results apparently showed that CD166 and CD5L are expressed in an arteriosclerosis lesion and leaked into plasma. That is, it is shown that lesion formation and progression can be evaluated by determining the CD166 and CD5L concentrations in plasma.

It is apparent that the present invention can be carried out in embodiments that are not specifically mentioned in the above descriptions or in the Examples. Therefore, modifications or changes to the present invention can be made. Thus, such modifications or changes fall within the scope of the claims of the present invention.

The present invention provides a technique for predicting atherosclerosis risk. The risk of developing atherosclerosis, the degree of the risk, and the probability of symptom progression can be examined and analyzed with the use of, as indicators, for example, the CD166 concentration or the concentrations of both CD166 and CD5L in blood. Accordingly, the present invention allows early detection, and appropriate judgment and diagnosis of the future risk of severe symptoms.

What is claimed is:

1. A method for evaluating a preventive or therapeutic effect of a test compound on atherosclerosis, said method comprising:
    administering a test compound to a subject in need of prevention of, or a therapeutic effect on, atherosclerosis; and
    determining the levels of CD166 expression and CD5L expression in samples taken from the subject over time,
    wherein the test compound is determined to be effective to treat or limit the occurance of atherosclerosis if the level of CD5L expression in the samples of the subject decreases over time; and
    wherein the test compound is determined to be effective to treat or limit the occurance of atherosclerosis if the level of CD 166 (ALCAM) expression, in the samples decreases over time.

2. The method according to claim 1, wherein the subject is a human.

3. The method according to claim 1, wherein the sample is serum or plasma.

4. The method according to claim 1 further comprises determining diagnosis or progression of atherosclerosis based on a change in the level of CD5L expression in the samples over time.

5. The method according to claim 4, which further comprises comparing the levels of CD166 and CD5L in samples of a group consisting of subjects in need of prevention or treatment of atherosclerosis to which the test compound has been administered with the levels of CD166 and CD5L in samples of a group consisting of subjects in need of prevention or treatment of atherosclerosis to which the test compound has not been administered.

6. The method of claim 4, further comprising determining diagnosis, development or progression of atherosclerosis based on both the change in the level of CD166 (ALCAM) expression in the samples over time and change in the level of CD5L expression in the samples over time.

7. The method of claim 6, wherein, if the level of CD166 (ALCAM) expression in the samples of a subject taken over the time remains higher than a reference value of CD166 from a healthy control group and, at the same time, the level of CD5L expression in the sample exceeds a reference value of CD5L, an onset of atherosclerosis is determined.

8. The method according to claim 1, which further comprises determining at least one level of other atherosclerosis markers in at least one of the samples.

9. The method of claim 1, wherein the test compound is determined to be effective if the level of CD5L expression in the samples of the subject decreases over time and the level of CD166 (ALCAM) expression in the samples of the subject decreases over time.

* * * * *

SEQUENCE LISTING

<160> NUMBER OF SEQ ID NOS: 43

<210> SEQ ID NO 1
<211> LENGTH: 583
<212> TYPE: PRT
<213> ORGANISM: Mus musculus

<400> SEQUENCE: 1

```
Met Ala Ser Lys Val Ser Pro Ser Cys Arg Leu Val Phe Cys Leu Leu
1               5                   10                  15

Ile Ser Ala Ala Val Leu Arg Pro Gly Leu Gly Trp Tyr Thr Val Asn
            20                  25                  30

Ser Ala Tyr Gly Asp Thr Ile Val Met Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Ser Leu Ser Glu Asn Tyr
                85                  90                  95

Thr Leu Ser Ile Ala Asn Ala Lys Ile Ser Asp Glu Lys Arg Phe Val
            100                 105                 110

Cys Met Leu Val Thr Glu Asp Asn Val Phe Glu Ala Pro Thr Leu Val
        115                 120                 125

Lys Val Phe Lys Gln Pro Ser Lys Pro Glu Ile Val Asn Lys Ala Pro
    130                 135                 140

Phe Leu Glu Thr Asp Gln Leu Lys Lys Leu Gly Asp Cys Ile Ser Arg
145                 150                 155                 160

Asp Ser Tyr Pro Asp Gly Asn Ile Thr Trp Tyr Arg Asn Gly Lys Val
                165                 170                 175

Leu Gln Pro Val Glu Gly Glu Val Ala Ile Leu Phe Lys Lys Glu Ile
            180                 185                 190

Asp Pro Gly Thr Gln Leu Tyr Thr Val Thr Ser Ser Leu Glu Tyr Lys
        195                 200                 205

Thr Thr Arg Ser Asp Ile Gln Met Pro Phe Thr Cys Ser Val Thr Tyr
    210                 215                 220

Tyr Gly Pro Ser Gly Gln Lys Thr Ile Tyr Ser Glu Gln Glu Ile Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Gln Cys Leu Gly
            260                 265                 270

Asn Gly Asn Pro Pro Glu Glu Phe Met Phe Tyr Leu Pro Gly Gln
        275                 280                 285

Pro Glu Gly Ile Arg Ser Ser Asn Thr Tyr Thr Leu Thr Asp Val Arg
    290                 295                 300

Arg Asn Ala Thr Gly Asp Tyr Lys Cys Ser Leu Ile Asp Lys Arg Asn
305                 310                 315                 320

Met Ala Ala Ser Thr Thr Ile Thr Val His Tyr Leu Asp Leu Ser Leu
                325                 330                 335

Asn Pro Ser Gly Glu Val Thr Lys Gln Ile Gly Asp Thr Leu Pro Val
            340                 345                 350

Ser Cys Thr Ile Ser Ala Ser Arg Asn Ala Thr Val Val Trp Met Lys
        355                 360                 365
```

```
Asp Asn Ile Arg Leu Arg Ser Ser Pro Ser Phe Ser Ser Leu His Tyr
    370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
                420                 425                 430

Ile Ile Cys His Val Glu Gly Phe Pro Lys Pro Ala Ile His Trp Thr
                435                 440                 445

Ile Thr Gly Ser Gly Ser Val Ile Asn Gln Thr Glu Glu Ser Pro Tyr
                450                 455                 460

Ile Asn Gly Arg Tyr Tyr Ser Lys Ile Ile Ser Pro Glu Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
                500                 505                 510

Asp Ile Ser Asp Glu Asn Arg Glu Lys Val Asn Asp Gln Ala Lys Leu
                515                 520                 525

Ile Val Gly Ile Val Val Gly Leu Leu Leu Ala Ala Leu Val Ala Gly
                530                 535                 540

Val Val Tyr Trp Leu Tyr Met Lys Lys Ser Lys Thr Ala Ser Lys His
545                 550                 555                 560

Val Asn Lys Asp Leu Gly Asn Met Glu Glu Asn Lys Lys Leu Glu Glu
                565                 570                 575

Asn Asn His Lys Thr Glu Ala
                580

<210> SEQ ID NO 2
<211> LENGTH: 352
<212> TYPE: PRT
<213> ORGANISM: Mus musculus

<400> SEQUENCE: 2

Met Ala Pro Leu Phe Asn Leu Met Leu Ala Ile Leu Ser Ile Phe Val
1               5                   10                  15

Gly Ser Cys Phe Ser Glu Ser Pro Thr Lys Val Gln Leu Val Gly Gly
                20                  25                  30

Ala His Arg Cys Glu Gly Arg Val Glu Val Glu His Asn Gly Gln Trp
            35                  40                  45

Gly Thr Val Cys Asp Asp Gly Trp Asp Arg Arg Asp Val Ala Val Val
        50                  55                  60

Cys Arg Glu Leu Asn Cys Gly Ala Val Ile Gln Thr Pro Arg Gly Ala
65                  70                  75                  80

Ser Tyr Gln Pro Pro Ala Ser Glu Gln Arg Val Leu Ile Gln Gly Val
                85                  90                  95

Asp Cys Asn Gly Thr Glu Asp Thr Leu Ala Gln Cys Glu Leu Asn Tyr
                100                 105                 110

Asp Val Phe Asp Cys Ser His Glu Glu Asp Ala Gly Ala Gln Cys Glu
            115                 120                 125

Asn Pro Asp Ser Asp Leu Leu Phe Ile Pro Glu Asp Val Arg Leu Val
        130                 135                 140

Asp Gly Pro Gly His Cys Gln Gly Arg Val Glu Val Leu His Gln Ser
145                 150                 155                 160
```

```
Gln Trp Ser Thr Val Cys Lys Ala Gly Trp Asn Leu Gln Val Ser Lys
                165                 170                 175

Val Val Cys Arg Gln Leu Gly Cys Gly Arg Ala Leu Leu Thr Tyr Gly
            180                 185                 190

Ser Cys Asn Lys Ser Thr Gln Gly Lys Gly Pro Ile Trp Met Gly Lys
        195                 200                 205

Met Ser Cys Ser Gly Gln Glu Ala Asn Leu Arg Ser Cys Leu Leu Ser
    210                 215                 220

Arg Leu Glu Asn Asn Cys Thr His Gly Glu Asp Thr Trp Met Glu Cys
225                 230                 235                 240

Glu Asp Pro Phe Glu Leu Lys Leu Val Gly Asp Thr Pro Cys Ser
                245                 250                 255

Gly Arg Leu Glu Val Leu His Lys Gly Ser Trp Gly Ser Val Cys Asp
            260                 265                 270

Asp Asn Trp Gly Glu Lys Glu Asp Gln Val Val Cys Lys Gln Leu Gly
        275                 280                 285

Cys Gly Lys Ser Leu His Pro Ser Pro Lys Thr Arg Lys Ile Tyr Gly
    290                 295                 300

Pro Gly Ala Gly Arg Ile Trp Leu Asp Asp Val Asn Cys Ser Gly Lys
305                 310                 315                 320

Glu Gln Ser Leu Glu Phe Cys Arg His Arg Leu Trp Gly Tyr His Asp
                325                 330                 335

Cys Thr His Lys Glu Asp Val Glu Val Ile Cys Thr Asp Phe Asp Val
            340                 345                 350

<210> SEQ ID NO 3
<211> LENGTH: 6
<212> TYPE: PRT
<213> ORGANISM: Mus musculus

<400> SEQUENCE: 3

Cys Ser Leu Ile Asp Lys
1               5

<210> SEQ ID NO 4
<211> LENGTH: 7
<212> TYPE: PRT
<213> ORGANISM: Mus musculus

<400> SEQUENCE: 4

Asp Val Ala Val Val Cys Arg
1               5

<210> SEQ ID NO 5
<211> LENGTH: 12
<212> TYPE: PRT
<213> ORGANISM: Mus musculus

<400> SEQUENCE: 5

Glu Leu Asn Cys Gly Ala Val Ile Gln Thr Pro Arg
1               5                   10

<210> SEQ ID NO 6
<211> LENGTH: 11
<212> TYPE: PRT
<213> ORGANISM: Mus musculus

<400> SEQUENCE: 6

Leu Val Asp Gly Pro Gly His Cys Gln Gly Arg
1               5                   10
```

```
<210> SEQ ID NO 7
<211> LENGTH: 14
<212> TYPE: PRT
<213> ORGANISM: Mus musculus

<400> SEQUENCE: 7

Val Glu Val Leu His Gln Ser Gln Trp Ser Thr Val Cys Lys
1               5                   10

<210> SEQ ID NO 8
<211> LENGTH: 10
<212> TYPE: PRT
<213> ORGANISM: Mus musculus

<400> SEQUENCE: 8

Ala Leu Leu Thr Tyr Gly Ser Cys Asn Lys
1               5                   10

<210> SEQ ID NO 9
<211> LENGTH: 6
<212> TYPE: PRT
<213> ORGANISM: Mus musculus

<400> SEQUENCE: 9

Ser Cys Leu Leu Ser Arg
1               5

<210> SEQ ID NO 10
<211> LENGTH: 11
<212> TYPE: PRT
<213> ORGANISM: Mus musculus

<400> SEQUENCE: 10

Leu Val Gly Gly Asp Thr Pro Cys Ser Gly Arg
1               5                   10

<210> SEQ ID NO 11
<211> LENGTH: 17
<212> TYPE: PRT
<213> ORGANISM: Mus musculus

<400> SEQUENCE: 11

Leu Val Gly Gly Asp Thr Pro Cys Ser Gly Arg Leu Glu Val Leu His
1               5                   10                  15

Lys

<210> SEQ ID NO 12
<211> LENGTH: 21
<212> TYPE: PRT
<213> ORGANISM: Mus musculus

<400> SEQUENCE: 12

Gly Ser Trp Gly Ser Val Cys Asp Asp Asn Trp Gly Glu Lys Glu Asp
1               5                   10                  15

Gln Val Val Cys Lys
            20

<210> SEQ ID NO 13
<211> LENGTH: 19
<212> TYPE: PRT
<213> ORGANISM: Mus musculus

<400> SEQUENCE: 13
```

```
Ile Trp Leu Asp Asp Val Asn Cys Ser Gly Lys Glu Gln Ser Leu Glu
1               5                   10                  15

Phe Cys Arg

<210> SEQ ID NO 14
<211> LENGTH: 7
<212> TYPE: PRT
<213> ORGANISM: Mus musculus

<400> SEQUENCE: 14

Asp Val Ala Val Val Cys Arg
1               5

<210> SEQ ID NO 15
<211> LENGTH: 12
<212> TYPE: PRT
<213> ORGANISM: Mus musculus

<400> SEQUENCE: 15

Glu Leu Asn Cys Gly Ala Val Ile Gln Thr Pro Arg
1               5                   10

<210> SEQ ID NO 16
<211> LENGTH: 11
<212> TYPE: PRT
<213> ORGANISM: Mus musculus

<400> SEQUENCE: 16

Leu Val Asp Gly Pro Gly His Cys Gln Gly Arg
1               5                   10

<210> SEQ ID NO 17
<211> LENGTH: 14
<212> TYPE: PRT
<213> ORGANISM: Mus musculus

<400> SEQUENCE: 17

Val Glu Val Leu His Gln Ser Gln Trp Ser Thr Val Cys Lys
1               5                   10

<210> SEQ ID NO 18
<211> LENGTH: 10
<212> TYPE: PRT
<213> ORGANISM: Mus musculus

<400> SEQUENCE: 18

Ala Leu Leu Thr Tyr Gly Ser Cys Asn Lys
1               5                   10

<210> SEQ ID NO 19
<211> LENGTH: 11
<212> TYPE: PRT
<213> ORGANISM: Mus musculus

<400> SEQUENCE: 19

Met Ser Cys Ser Gly Gln Glu Ala Asn Leu Arg
1               5                   10

<210> SEQ ID NO 20
<211> LENGTH: 6
<212> TYPE: PRT
<213> ORGANISM: Mus musculus

<400> SEQUENCE: 20

Ser Cys Leu Leu Ser Arg
```

<210> SEQ ID NO 21
<211> LENGTH: 11
<212> TYPE: PRT
<213> ORGANISM: Mus musculus

<400> SEQUENCE: 21

Leu Val Gly Gly Asp Thr Pro Cys Ser Gly Arg
1               5                   10

<210> SEQ ID NO 22
<211> LENGTH: 17
<212> TYPE: PRT
<213> ORGANISM: Mus musculus

<400> SEQUENCE: 22

Leu Val Gly Gly Asp Thr Pro Cys Ser Gly Arg Leu Glu Val Leu His
1               5                   10                  15

Lys

<210> SEQ ID NO 23
<211> LENGTH: 19
<212> TYPE: PRT
<213> ORGANISM: Mus musculus

<400> SEQUENCE: 23

Ile Trp Leu Asp Asp Val Asn Cys Ser Gly Lys Glu Gln Ser Leu Glu
1               5                   10                  15

Phe Cys Arg

<210> SEQ ID NO 24
<211> LENGTH: 8
<212> TYPE: PRT
<213> ORGANISM: Mus musculus

<400> SEQUENCE: 24

Glu Gln Ser Leu Glu Phe Cys Arg
1               5

<210> SEQ ID NO 25
<211> LENGTH: 7
<212> TYPE: PRT
<213> ORGANISM: Mus musculus

<400> SEQUENCE: 25

Asp Val Ala Val Val Cys Arg
1               5

<210> SEQ ID NO 26
<211> LENGTH: 12
<212> TYPE: PRT
<213> ORGANISM: Mus musculus

<400> SEQUENCE: 26

Glu Leu Asn Cys Gly Ala Val Ile Gln Thr Pro Arg
1               5                   10

<210> SEQ ID NO 27
<211> LENGTH: 25
<212> TYPE: PRT
<213> ORGANISM: Mus musculus

<400> SEQUENCE: 27

```
Leu Val Asp Gly Pro Gly His Cys Gln Gly Arg Val Glu Val Leu His
1               5                   10                  15
Gln Ser Gln Trp Ser Thr Val Cys Lys
            20                  25
```

<210> SEQ ID NO 28
<211> LENGTH: 14
<212> TYPE: PRT
<213> ORGANISM: Mus musculus

<400> SEQUENCE: 28

```
Val Glu Val Leu His Gln Ser Gln Trp Ser Thr Val Cys Lys
1               5                   10
```

<210> SEQ ID NO 29
<211> LENGTH: 10
<212> TYPE: PRT
<213> ORGANISM: Mus musculus

<400> SEQUENCE: 29

```
Ala Leu Leu Thr Tyr Gly Ser Cys Asn Lys
1               5                   10
```

<210> SEQ ID NO 30
<211> LENGTH: 11
<212> TYPE: PRT
<213> ORGANISM: Mus musculus

<400> SEQUENCE: 30

```
Met Ser Cys Ser Gly Gln Glu Ala Asn Leu Arg
1               5                   10
```

<210> SEQ ID NO 31
<211> LENGTH: 6
<212> TYPE: PRT
<213> ORGANISM: Mus musculus

<400> SEQUENCE: 31

```
Ser Cys Leu Leu Ser Arg
1               5
```

<210> SEQ ID NO 32
<211> LENGTH: 11
<212> TYPE: PRT
<213> ORGANISM: Mus musculus

<400> SEQUENCE: 32

```
Leu Val Gly Gly Asp Thr Pro Cys Ser Gly Arg
1               5                   10
```

<210> SEQ ID NO 33
<211> LENGTH: 17
<212> TYPE: PRT
<213> ORGANISM: Mus musculus

<400> SEQUENCE: 33

```
Leu Val Gly Gly Asp Thr Pro Cys Ser Gly Arg Leu Glu Val Leu His
1               5                   10                  15
Lys
```

<210> SEQ ID NO 34
<211> LENGTH: 21
<212> TYPE: PRT
<213> ORGANISM: Mus musculus -continued

<400> SEQUENCE: 34

Gly Ser Trp Gly Ser Val Cys Asp Asp Asn Trp Gly Glu Lys Glu Asp
1               5                   10                  15

Gln Val Val Cys Lys
            20

<210> SEQ ID NO 35
<211> LENGTH: 19
<212> TYPE: PRT
<213> ORGANISM: Mus musculus

<400> SEQUENCE: 35

Ile Trp Leu Asp Asp Val Asn Cys Ser Gly Lys Glu Gln Ser Leu Glu
1               5                   10                  15

Phe Cys Arg

<210> SEQ ID NO 36
<211> LENGTH: 12
<212> TYPE: PRT
<213> ORGANISM: Mus musculus

<400> SEQUENCE: 36

Glu Leu Asn Cys Gly Ala Val Ile Gln Thr Pro Arg
1               5                   10

<210> SEQ ID NO 37
<211> LENGTH: 11
<212> TYPE: PRT
<213> ORGANISM: Mus musculus

<400> SEQUENCE: 37

Leu Val Asp Gly Pro Gly His Cys Gln Gly Arg
1               5                   10

<210> SEQ ID NO 38
<211> LENGTH: 14
<212> TYPE: PRT
<213> ORGANISM: Mus musculus

<400> SEQUENCE: 38

Val Glu Val Leu His Gln Ser Gln Trp Ser Thr Val Cys Lys
1               5                   10

<210> SEQ ID NO 39
<211> LENGTH: 11
<212> TYPE: PRT
<213> ORGANISM: Mus musculus

<400> SEQUENCE: 39

Met Ser Cys Ser Gly Gln Glu Ala Asn Leu Arg
1               5                   10

<210> SEQ ID NO 40
<211> LENGTH: 6
<212> TYPE: PRT
<213> ORGANISM: Mus musculus

<400> SEQUENCE: 40

Ser Cys Leu Leu Ser Arg
1               5

<210> SEQ ID NO 41
<211> LENGTH: 11
<212> TYPE: PRT

-continued

```
<213> ORGANISM: Mus musculus

<400> SEQUENCE: 41

Leu Val Gly Gly Asp Thr Pro Cys Ser Gly Arg
1               5                   10

<210> SEQ ID NO 42
<211> LENGTH: 17
<212> TYPE: PRT
<213> ORGANISM: Mus musculus

<400> SEQUENCE: 42

Leu Val Gly Gly Asp Thr Pro Cys Ser Gly Arg Leu Glu Val Leu His
1               5                   10                  15

Lys

<210> SEQ ID NO 43
<211> LENGTH: 19
<212> TYPE: PRT
<213> ORGANISM: Mus musculus

<400> SEQUENCE: 43

Ile Trp Leu Asp Asp Val Asn Cys Ser Gly Lys Glu Gln Ser Leu Glu
1               5                   10                  15

Phe Cys Arg
```